US005763496A

United States Patent [19]
Holland

[11] Patent Number: 5,763,496
[45] Date of Patent: Jun. 9, 1998

[54] PREVENTION OF ATHEROSCLEROSIS USING NADPH OXIDASE INHIBITORS

[75] Inventor: James Arthur Holland, Bath, N.Y.

[73] Assignee: The Research Foundation of State University of New York, Albany, N.Y.

[21] Appl. No.: 562,767

[22] Filed: Nov. 27, 1995

[51] Int. Cl.$^6$ .......... A61K 31/12; A61K 31/11; A61K 31/075; A61K 31/06
[52] U.S. Cl. .......... 514/689; 514/568; 514/699; 514/717; 514/731
[58] Field of Search .......... 514/689, 568, 514/699, 717, 824, 731

[56] References Cited

U.S. PATENT DOCUMENTS 5,244,916  9/1993  Bokoch .......... 514/460

FOREIGN PATENT DOCUMENTS

| 0 551 662 A1 | of 1993 | European Pat. Off. |
| 4109627 | 9/1992 | Germany |
| 6135880 | 5/1994 | Japan |
| 06227977 | 8/1994 | Japan |
| 07165575 | 6/1995 | Japan |
| 91/17763 | of 1991 | WIPO |
| WO9513063 | 5/1995 | WIPO |

OTHER PUBLICATIONS

Handley DA, Saunders RN. Drug Development Research 7, pp. 361–375, 1986.
Munro JM, Cotran RS. Lab. Invest. 58(3), pp. 249–261, 1988.
Gallin JI, Goldstein, IM, Snyderman R. Inflammation:Basic Principles and Clinical Correlates. Second edition. Raven Press. New York. p. 1, 1992.
Pritchard KA Jr. et al. Arteriosclerosis and Thrombosis. 11 (5) 1175–81, Sep. 1991.
Kalra VA et al. Journal of Cellular Physiology, 160 (1) 154–62, Jul. 1994.
"Human Fat Cells Possess a Plasma Membrane-bound $H_2O_2$-generating System . . . ", Krieger–Brauer et al., *J. Clin. Invest.*, 86, 1006–1013 (1992).
"Flow–Cytometric Characterization of Stimulation, Free Radical Formation . . . ", Burow et al., *European Journal of Cell Biology*, 43, 128–133 (1987).
"Antiarthritic Activity of the Newly Developed Neutrophil Oxidative . . . ", 'T Hart et al., *Free Radical Biology & Medicine*, 9, 127–131 (1990).
"Metabolic Activation of Natural Phenols into Selective Oxidative . . . ", Simons et al., *Free Radical Biology & Medicine*, 8, 251–258 (1990).
"Regulation of Phagocyte Oxygen Radical Production by the GTP-Binding Protein Rac 2", Knaus et al. *Science*, 254, 1512–1515 (1991).
"Characteristics of the Inhibition of NADPH Oxidase Activation in . . . ", Stolk et al., *Am. J. Respir. Cell. Mol. Biol.*, 11, 95–102 (1994).
"The Effect of Inhibitors of Free Radical Generating–Enzymes . . . ", Wilkins et al., *Biochim. Biophys. Acta*, 1211, 69–78 (1994).
"Effects of Apocynin, a Drug Isolated from the Roots of *Picrorhiza–kurroa* . . . ", Engels et al., *FEBS Lett.*, 305, 254–256 (1992).
"Effects of Nafenopin, Diphenylhydantoin, Phenobarbitone and Some Acetylenes . . . ", Arch et al., *Int. J. Obes.*, 4, 1–10 (1980).
"Improved Methods for the Solubilization and Assay of Hepatic 3–Hydroxy–3–methylglutaryl . . . ", Edwards et al., *J. Lipid Res.*, 20 40–46 (1979).
Senaratne et al. "Lovastatin prevents the impairment of endothelium dependent . . . " *Cardivasc. Res.* 25, 568–578 (1991).
Goldstein et al. "Regulation of low–density lipoprotein receptors:implications . . . " *Circulation* 76, 504–507 (1987).
Wasielewski "Lovastatin verzogert Athersklerose . . . " *A. Allg. Med.* 68, 987 (1993).
Aviram et al. "Lovastatin Inhibits Low–Density Lipoprotein Oxidation and Alters Its Fluidity . . . " *Metabolism* 41, 229–235 (1992).
Weber et al. "Antioxidants inhibit monocyte adhesion by suppressing nuclear . . . " *Arterioscler. Throm.* 14, 1665–1673 (1994).
Bors et al., "Antioxidants: their function and mechanism as radical scavengers" *Proc. Int. Conf. Superoxide* 1, 38–43 (1982).
Keaney et al. "Atherosclerosis, Oxidative Stress, and Antioxidant Protection . . . " *Prog. Cardivasc. Dis.* 38, 129–154 (1995).
Day et al. "Hypercholesterolemia and simvastatin therapy: Effects on cell membrane . . . " *Clin. Chem.* 21, S137 (1995).

*Primary Examiner*—C. Warren Ivy
*Assistant Examiner*—Evelyn Huang
*Attorney, Agent, or Firm*—Heslin & Rothenberg, P.C.

[57] ABSTRACT

A method for the prevention and treatment of atherosclerosis and its related diseases in mammals is provided, in which an NADPH oxidase inhibitor is administered to mammals. The NADPH oxidase inhibitor prevents the production of reactive oxygen species upon exposure of endothelial cells to atherogenic LDL levels, resulting in decreased endocytosis and vascular hyperpermeability. Apocynin is a preferred NADPH oxidase inhibitor. Additionally, there is provided a diagnostic method for predicting the risk to an individual of atherosclerotic-related diseases.

5 Claims, 3 Drawing Sheets

PREVENTION OF ATHEROSCLEROSIS USING NADPH OXIDASE INHIBITORS

STATEMENT AS TO RIGHTS UNDER FEDERALLY SPONSORED RESEARCH

This invention was made with support from the National Institutes of Health (Grant No. 5R01 HL49573) and from the Department of Veterans Affairs (Merit Review 0002). The United States government may have certain rights in the invention.

FIELD OF THE INVENTION

The present invention relates to therapeutic methods for the prevention and treatment of atherosclerosis and diseases resulting from endothelial hyperpermeability. More particularly, the present invention relates to the prevention and treatment of these diseases through the administration of an NADPH oxidase inhibitor.

BACKGROUND OF THE INVENTION

Atherosclerosis with its sequelae of heart attacks, strokes, and peripheral vascular disease is the leading cause of death in the United States with over 800,000 deaths per year. Excluding accidents, suicides, and homicides, atherosclerotic-related diseases account for nearly 50% of all deaths. Epidemiologic studies show that a large percentage of those afflicted have an elevation in plasma low density lipoprotein (LDL) levels. LDL carries cholesterol from the liver to body tissues. An elevated cholesterol level (hypercholesterolemia) is commonly associated with an elevation in LDL levels. High blood cholesterol levels, specifically LDL-cholesterol, increase risk for coronary heart disease (CHD), whereas lowering total cholesterol and LDL-cholesterol levels reduces CHD risk.

Many pharmaceutical agents have been developed to treat or prevent atherosclerosis and its complications by controlling abnormally high blood LDL levels or lowering cholesterol levels. The most widely known of these agents include nicotinic acid, clofibrate, dextrothyroxine sodium, neomycin, beta-sitosterol, probucol, cholestyramine and HMG-CoA reductase inhibitors, such as lovastatin and simvastatin. However, the usefulness of these agents is limited by the frequent occurrence of acute side effects. Such side effects may include intense cutaneous flush, pruritus, increased atrial fibrillation, gastrointestinal irritation, hepatotoxicity, cardiac arrhythmias, nausea, diarrhea, weight gain, skin rash, alopecia, impotence, abdominal pain, diarrhea, nausea, eosinophilia, skin rash, mucoskeletal pain, blurred vision, mild anemia, leukopenia, the enhancement of gallstones, constipation, and impaction. Moreover, there is only partial correlation between lowering of serum cholesterol and the reduction of atherosclerosis. Not all patients with atherosclerotic heart disease have high cholesterol and not all patients with high cholesterol have atherosclerotic heart disease.

The pathobiology of atherosclerosis indicates a major role for vascular endothelial involvement. Perturbation of the endothelium, without overt death and loss of endothelial cells, with resultant change in endothelial permeability to various blood materials is an important feature in the development of atherosclerotic lesions. Materials contained in the blood subsequently pass through those endothelial tissues and accumulate in the intima of the arterial wall. Even a moderate increase in endothelial permeability (hyperpermeability) is accompanied by a significant increase in the incidence of atherosclerotic events.

One mechanism by which vascular hyperpermeability can occur in the presence of an intact endothelium is increased endothelial endocytosis due to perturbation of the endothelium. The endothelium can be perturbed by various conditions, including high levels of low density lipoprotein (LDL) in the bloodstream and shear stress, as occurs in hypertension. Diabetes mellitus and smoking can also give rise to perturbation of the endothelium. I have conducted studies in which human vascular endothelial cells (EC) were exposed to high LDL concentrations (up to 300 mg/dL cholesterol) for a prolonged period. The results, as demonstrated by stability of cell count for instance, indicate that EC death and loss do not occur in humans during the promotion of atherosclerotic plaque formation by LDL.

Endothelial perturbation initially occurs, resulting in increased endocytosis and LDL accumulation in the subendothelial space. That is, exposure to high LDL levels induces heightened EC endocytosis. Studies indicate that exposure to LDL, in concentration ranges that are considered from epidemiologic studies to be atherogenic (endothelial cells exposed to 160–240 mg/dL LDL cholesterol over 2–4 days, for example), is necessary for exaggerated endocytosis. Another key finding is that once heightened endocytosis develops, it persists. Such a persistent change in EC functional state is consistent with the endothelial perturbation, or vascular hyperpermeability, concept.

Endocytosis is a fundamental, apparently ubiquitous, cellular event. During endocytosis, a segment of plasma membrane is interiorized to form a vesicle that migrates into the cytoplasm. This vesicle may fuse with cytoplasmic lysosomes or participate in transcellular transport via transcytosis. LDL in vesicles fused to lysosomes is degraded and lipids, including arachidonic acid, are released into the cell. The endocytosis regulatory mechanism is not well understood, but my studies demonstrate that reactive oxygen species, such as $H_2O_2$ and $O_2$, modulate heightened EC endocytosis. Cells generate reactive oxygen species (ROS) as byproducts of normal cellular metabolism. Perturbed endothelial cells increase reactive oxygen species production via the activation of nicotinamide adenine dinucleotide phosphate (NADPH) oxidase.

NADPH oxidase is an enzyme that has been well characterized in phagocytic cells, but has not been previously identified in endothelial cells. I have demonstrated that it occurs in endothelial cells. Activation of NADPH oxidase results in the transfer of electrons from NADPH to oxygen, resulting in the generation of reactive oxygen species (ROS) such as $O_2^-$ and $H_2O_2$. The active form of the oxidase is a complex assembled from membrane-bound proteins that include cytochrome $b_{558}$ (composed of $p91_{[phox]}$) and $p22_{[phox]}$ and cytosolic components, of which four have been characterized, $p40_{[phox]}$, $p47_{[phox]}$, $p67_{[phox]}$ and GTP-binding protein. Cytochrome b is a 22 kD peptide which tightly binds to a highly glycosylated 91 kD subunit. The 91 kD peptide is an integral membrane protein that serves to anchor the 22 kD peptide.

It is known that inheritable abnormalities of the NADPH oxidase enzyme complex result in Chronic Granulomatous Disease (CGD), a congenital disorder in which phagocytic cells are unable to generate reactive oxygen species in response to microorganisms. Studies on CGD, in which NADPH oxidase activity is insufficient or absent, have shown that genetic variants of NADPH oxidase exist. There have been no studies, though, to identify NADPH oxidase genetic variants that produce excessive amounts of reactive oxygen species. If such variants exist and are common in our population, then people inheriting these genetic variants are at higher risk of heart attacks, strokes, and peripheral vascular diseases.

The membrane-bound enzyme, NADPH oxidase, exists in an inactive form in quiescent cells. Upon cell perturbation, the enzyme complex assembles and is converted into an active state causing intensified reactive oxygen species generation (oxidative burst). Studies attempting to delineate the NADPH oxidase activation mechanism indicate that unsaturated fatty acids, including arachidonic acid, directly activate NADPH oxidase. To ascertain if arachidonic acid activates the NADPH oxidase found in endothelial cells, studies were carried out in which cells were directly exposed to increasing arachidonic acid concentrations and reactive oxygen species generation was measured. For these studies, EC were incubated with 1 to 25 µM arachidonic acid and $H_2O_2$ generation measured. It was shown that arachidonic acid both induces EC $H_2O_2$ generation and promotes heightened EC endocytosis.

One explanation for the correlation between high LDL and atherosclerosis based on the above information is that LDL's may provide EC with a source of arachidonic acid. At an intracellular threshold level, cytosolic free arachidonic acid converts NADPH oxidase from a dormant to an active state. Activated phospholipase $A_2$ also provides arachidonic acid for NADPH oxidase activation.

Evidence from my experiments indicates that reactive oxygen species modulate heightened endocytosis, a characteristic of atherosclerosis, and that NADPH oxidase is the major cellular source. Although NADPH oxidase inhibitors are claimed to be effective in treating inflammatory conditions, they have not been heretofore suggested to treat diseases such as atherosclerosis, whose initial phase is characterized by increased endocytosis and vascular hyperpermeability. For example, European patent application 551662 discloses the use of NADPH oxidase inhibitors to control acute and chronic inflammations of the airways, joints, and blood vessels. Such inflammations of the vessels include those arterioscleroses that are of inflammatory origin, but the EP application does not envision atherosclerosis, because atherosclerosis is initiated by a metabolic condition, not by inflammation.

The use of 4-hydroxy-3-methoxyacetophenone (trivial name, apocynin) as an NADPH oxidase inhibitor is known, and it has been suggested to be of utility in treating inflammatory diseases. Apocynin is a natural phenol isolated from the root of the plant Picrorhiza kurroa, which grows in the Himalaya mountains. Extracts of Picrorhiza kurroa have been used in traditional medicine in Southeast Asia for the treatment of diseases connected with inflammation and for the treatment of a variety of conditions including liver and lung diseases, fever, skin lesions, worm infections, rheumatic disease, urinary disorders, heart failure, and snake and scorpion bites. A more recent reference [Engels et al. FEBS Lett., 305, 254–56 (1992)] suggests that apocynin may also be useful in preventing thrombosis. However, neither apocynin nor any other NADPH oxidase inhibitor has been shown to prevent atherosclerosis or vascular hyperpermeability attributable to heightened EC endocytosis and high LDL concentrations.

A method that is effective in most patients, that prevents and treats atherosclerosis and its associated diseases, and that avoids patient-deterring side effects would represent a substantial advance toward eliminating a major cause of death in this country. A method employing a readily available medicament that has already been used in humans would present additional significant advantages in the prevention and treatment of atherosclerosis and related diseases. In addition, a diagnostic method for predicting an individual's potential risk of developing atherosclerosis is highly desirable.

SUMMARY OF THE INVENTION

The present invention relates to the surprising discovery of an effective method and composition for treating and preventing atherosclerosis in mammals. The present invention provides a method for the therapeutic use of an NADPH oxidase inhibitor, preferably apocynin, for the treatment and prevention of conditions resulting from endothelial hyperpermeability, such as atherosclerosis. Inhibition of NADPH oxidase activation in endothelial cells diminishes vascular hyperpermeability. Other conditions associated with vascular hyperpermeability can also be treated or prevented by administering an NADPH oxidase inhibitor such as apocynin.

In one aspect, the present invention relates to methods for preventing or treating a condition resulting from endothelial hyperpermeability. The method comprises administering to a mammal suffering from a condition resulting from endothelial hyperpermeability a therapeutically effective amount of an NADPH oxidase inhibitor. A preferred inhibitor is apocynin. Conditions that result from vascular hyperpermeability include atherosclerosis and diseases related to atherosclerosis, including heart attacks, strokes, and peripheral vascular disease. By the terms "preventing" and "treating" applicant does not intend that the disease or condition must be completely abolished, only that there is some amelioration, i.e. that its normal course be substantially diminished, so that an improvement over the expected symptomology is clinically observable.

In another aspect, the present invention relates to a method for predicting the risk of a human patient to diseases, such as atherosclerosis, that result from endothelial hyperpermeability. The method comprises identifying a patient having elevated NADPH oxidase activity. Elevated NADPH oxidase activity is defined for the purpose of the present invention as more than 10% above the range found in paired controls. Such identification is preferably done by measuring the NADPH oxidase activity in white blood cells (polymorphonuclear leukocytes) of the patient. Polymorphonuclear leukocyte (PMN) NADPH oxidase activity may be measured using flow cytometry with 2,7-dichlorofluorescein diacetate as the indicator. After identifying such a patient, administration of an NADPH oxidase inhibitor, such as apocynin, can be recommended for preventing or treating atherosclerosis and its related diseases.

BRIEF DESCRIPTION OF THE DRAWINGS

These and other objects, features and advantages of the invention will be evident from the following detailed description when read in conjunction with the accompanying drawings in which.

DETAILED DESCRIPTION OF THE INVENTION

Figure 1:
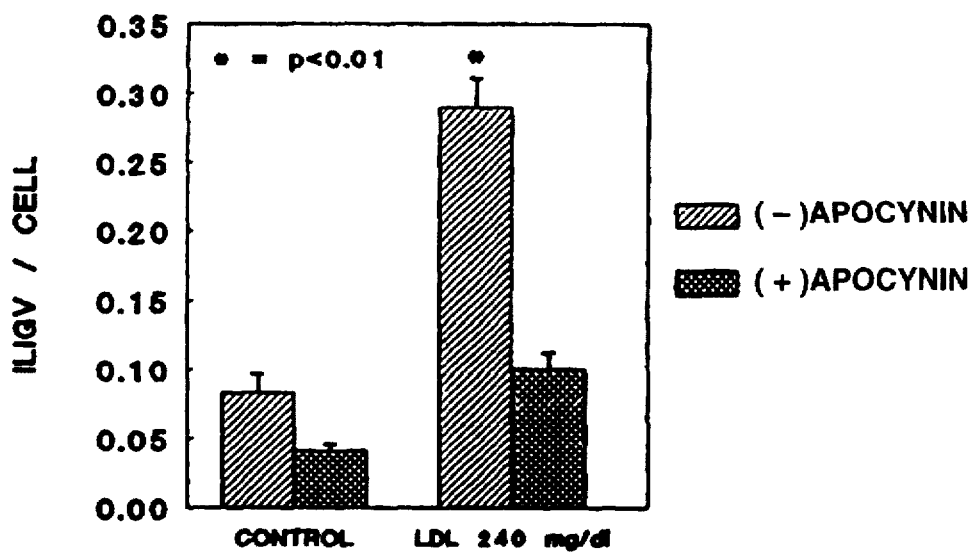
FIG. 1 is a graph of optical density from fluorescence spectroscopy, measured as "ILIGV", per cell for four test groups of endothelial cells, showing the effect of apocynin on high-LDL induction of endothelial cell peroxide production.

The present invention provides a method for preventing and treating atherosclerosis and diseases related thereto, conditions associated with increased endothelial permeability. According to the invention, the administration of an NADPH oxidase inhibitor, such as apocynin, inhibits NADPH oxidase activation in endothelial cells. The activation of NADPH oxidase is the major cellular source of the oxidative burst (an intensified generation of reactive oxygen species), which is associated with serum LDL levels that are known to be atherogenic. The oxidative burst modulates heightened endocytosis and endothelial hyperpermeability.

The present invention additionally provides a diagnostic method for predicting the risk of atherosclerosis-related diseases by measuring NADPH oxidase activity. Individuals with a clinically documented history of atherosclerotic-related diseases, or strong family history thereof, have higher NADPH oxidase activity than people without any medical or family history of the diseases.

A preferred NADPH oxidase inhibitor in the present invention is apocynin, but the method of the invention is not limited to apocynin, and a variety of other chemicals known to inhibit NADPH oxidase in endothelial cells may be used, as will be obvious to those skilled in the art. In the case of apocynin, the intact molecule (the ortho-methoxy phenol) appears to be effective as an inhibitor, and in addition, an effective intermediate in one mode of inhibition is the catechol that arises from enzymic demethylation at the 3-position. Thus other metabolic precursors to catechols, as well as the catechols themselves, are effective inhibitors of NADPH oxidase and are contemplated within the invention. Examples of other types of NADPH oxidase inhibitors that may be useful include, but are not limited to, isoprenylation inhibitors such as lovastatin and compactin (see U.S. Pat. No. 5,224,916), benzofuranyl- and benzothienyl thioalkane carboxylates (see EP appln 551,662), and cytochrome $b_{558}$ fragments and their analogs (see PCT application WO 91/17763). The pertinent parts of the foregoing three patent documents are incorporated herein by reference.

Although it is believed that most of the known NADPH oxidase inhibitors act by interfering with the assembly of the active complex, the term NADPH oxidase inhibitor, as used herein, is not intended to be restricted as to mechanism. Any substance that inhibits the NADPH oxidase-catalyzed generation of active oxygen species is encompassed by the term "NADPH oxidase inhibitor". The claimed method for treating atherosclerosis by NADPH oxidase inhibitors can be distinguished from the known methods for treating atherosclerosis employing compounds that (although the mechanism was previously unknown) happen also to be NADPH inhibitors. The claimed method can employ doses of known inhibitors (e.g. lovastatin) that would be therapeutically ineffective to reduce LDL, i.e. that produce less than 10% lowering of serum LDL.

Alternatively, the claimed method employs inhibitors that are targeted to the NADPH oxidase complex in that they have a lower $IC_{50}$ vs human NADPH oxidase than vs human HMG-CoA reductase. For the purpose of the present invention, the $IC_{50}$ is defined, according to standard practice, as the concentration of inhibitor required to inhibit the enzyme in question by 50%. The $IC_{50}$ vs human NADPH oxidase is measured as described in U.S. Pat. No. 5,244,916 column 11–12; the $IC_{50}$ vs human HMG-CoA reductase is measured as described by Edwards et al. [*J. Lipid Res.* 20, 40–46 (1979)], both of which are incorporated herein by reference. A brief description of the HMG-CoA reductase measurement is as follows:

A fragment of human liver is homogenized at 4° C. in 25 mL of buffer A (0.1M sucrose, 0.05M KCl, 0.04M potassium phosphate and 0.03M potassium EDTA; pH 7.2) and the microsomes are prepared as described by Edwards and Gould [*J. Biol. Chem.* 247, 1520–1524 (1972)]. The microsomes are resuspended in buffer A to a concentration of approximately 82 mg protein/mL, solid DTT is added to a final concentration of 10 mM and the microsomes are homogenized. Three mL aliquots of the microsome suspension are frozen in glass tubes at a rate of 6°–8° C. per min as described by Heller and Gould [*Biochem. Biophys. Res. Comm.* 50, 859–865 (1973)], and stored at −20° C. for up to two months.

For optimal solubilization of the reductase the frozen microsomes are allowed to thaw at room temperature before addition of an equal volume of 50% glycerol in buffer B (buffer A plus 10 mM DTT) preheated to 37° C. The suspension is rehomogenized and then incubated at 37° C. for 60 minutes. The suspension is diluted threefold with buffer B preheated to 37° C. to a final glycerol concentration of 8.3%, rehomogenized and centrifuged at 100,000 g for 60 minutes at 25° C. The supernatant, containing solubilized HMG-CoA reductase, is removed and used immediately.

The activity of the solubilized HMG-CoA reductase is determined at 37° C. in a total volume of 0.5 mL using a spectrophotometer. The cell path length is 1.0 cm. The rate of oxidation of NADPH is initially determined in the absence of HMG-CoA and this blank value, if any, is subtracted from the rate obtained with both substrates.

Maximum activity is obtained by assaying the enzyme in buffer C (0.2M KCl, 0.16M potassium phosphate, 0.004 MEDTA, and 0.01 MDTT, pH 6.8) together with 0.2 mM NADPH and 0.1 mM RS-HMG-CoA. One unit of enzyme activity is defined as the amount required to oxidize 2 nmol NADPH per minute. Hence, one unit is equivalent to the synthesis of 1 nmol mevalonate per minute.

Inhibition is measured in buffer C. The results are expressed as the 50% inhibitory concentration ($IC_{50}$) for the test substance. Six to ten test substance concentrations, separated by approximately ½ log, are tested in duplicate. The test substances are dissolved in buffer C for addition to the incubations. The $IC_{50}$ is calculated by linear interpolation.

A class of inhibitors that inhibits NADPH oxidase but does not block isoprenylation can be distinguished by the fact that they effect statistically equivalent inhibition of human NADPH oxidase in the presence and absence of mevalonate (see U.S. Pat. No. 5,244,916, column 14, line 60 to column 15, line 30).

In Vitro Apocynin Experiments

Experiments were performed in vitro using a high LDL endothelial cell tissue culture system. Endothelial cells were isolated from human umbilical cord veins and placed in experimental wells to which LDL media were added. The tissue culture components and chemicals are commercially available and were obtained from Sigma, Worthington, and Gibco. LDL were isolated from human blood plasma. Apocynin is available from Aldrich Chemical Co. (USA).

Figure 2:
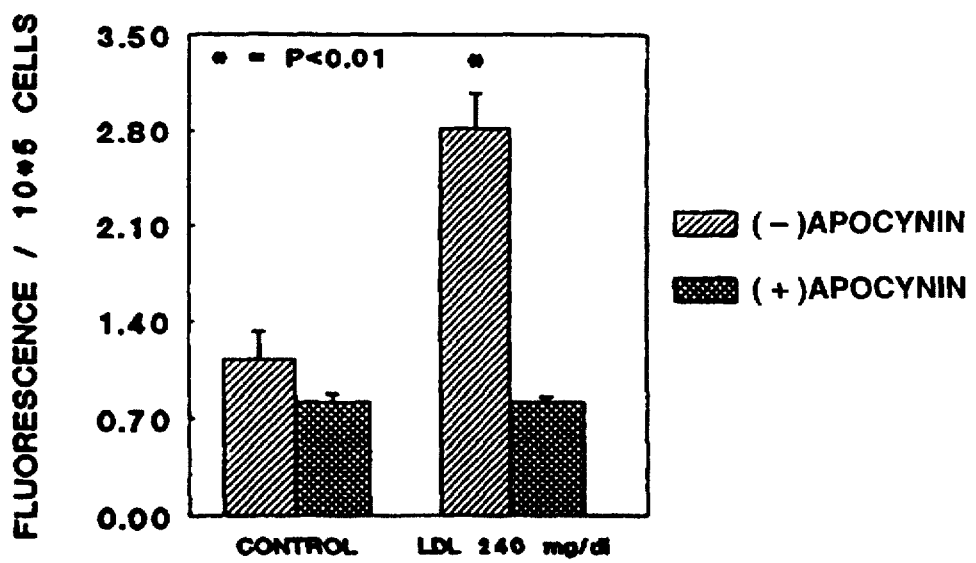
FIG. 2 is a graph of fluorescence per $10^5$ cells for four test groups of endothelial cells, showing the effect of apocynin on high-LDL induction of endothelial cell endocytosis.

Studies were conducted using apocynin to block NADPH oxidase activation and thereby prevent heightened endocytosis. Apocynin interferes with the assembly of a functional NADPH oxidase enzyme complex. For apocynin studies, EC were incubated with 240 mg/dL LDL cholesterol in the presence and absence of 100 μg/mL apocynin. As shown in FIGS. 1 and 2, apocynin effectively inhibits (1) the induction of $H_2O_2$ production and (2) endocytosis alterations associated with high concentrations of LDL.

As mentioned above, arachidonic acid activates EC NADPH oxidase directly, by inducing EC $H_2O_2$ generation; exposure to arachidonic acid promotes heightened EC endocytosis.

Figure 3:
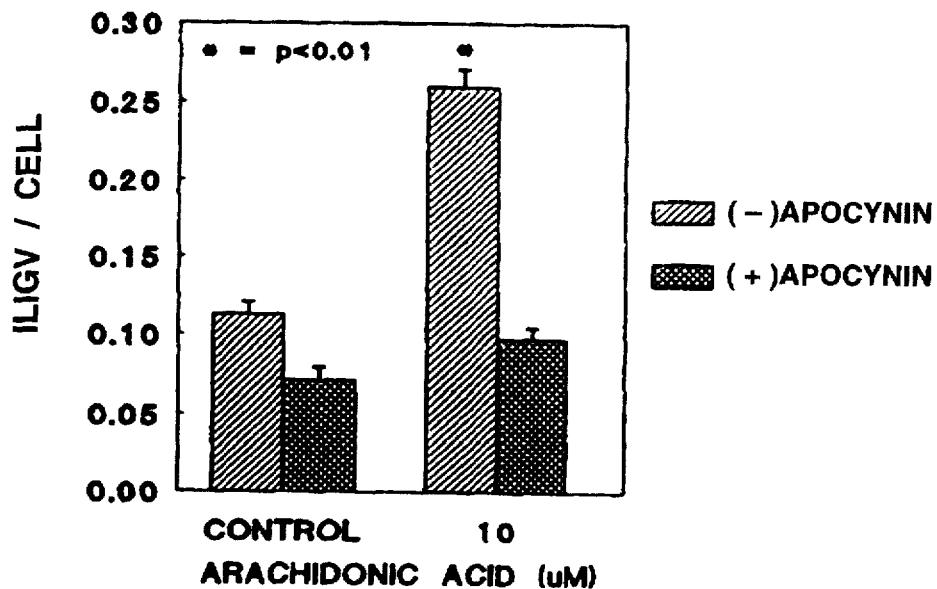
FIG. 3 is a graph of optical density from fluorescence spectroscopy, measured as "ILIGV", per cell for four test groups of endothelial cells, showing the effect of apocynin on arachidonic acid induction of endothelial cell peroxide production.

Further support that the arachidonic acid-induced oxidative burst results from NADPH oxidase activation is provided from the results of the following test in which apocynin was used to block NADPH oxidase activation. EC were incubated with 10 μM arachidonic acid in the presence and absence of 100 μg/mL apocynin. FIG. 3 shows that apocynin markedly reduces arachidonic acid-induced EC $H_2O_2$ generation.

Additional studies were conducted to provide further insight into the mechanism of NADPH oxidase activation. The cellular enzyme, phospholipase $A_2$ ($PLA_2$) hydrolyses membrane phospholipids releasing arachidonic acid intracellularly. $PLA_2$ inhibition by its antagonist, p-bromophenacyl bromide (BPB), suppresses the rise in cytosolic free arachidonic acid and limits this secondary messenger for NADPH oxidase activation. Thus, $PLA_2$ inhibition blocks LDL-EC NADPH oxidase activation. In these studies, EC were exposed to 240 mg/dL LDL-cholesterol with and without 10 μM BPB. BPB markedly diminished LDL-EC reactive oxygen species production. Activation of $PLA_2$ is provided in part in the LDL-EC system by the oxidation of ω-6 fatty acids with $H_2O_2$.

$PLA_2$ is a $Ca^{2+}$-dependent enzyme. Likewise, $Ca^{2+}$ is required for NADPH oxidase activation in intact cells. $PLA_2$-mediated arachidonic acid release parallels extracellular $Ca^{2+}$ concentration. Studies were conducted to determine whether LDL-EC have increased cellular $Ca^{2+}$ influx. In these studies, EC were incubated with increasing LDL levels (30 to 240 mg/dL cholesterol), and cellular $Ca^{2+}$ influx was measured employing a $^{45}Ca^{2+}$ uptake assay as described by Lewis et al. [*J. Clin. Invest.*, 82, 2045–2055 (1988)]. It was found that LDL-EC promote a dose-dependent rise in cellular $Ca^{2+}$ influx. LDL may induce $Ca^{2+}$ influx by EC exposure to $H_2O_2$, causing cellular permeabilization to $Ca^{2+}$ and resulting in an intracellular calcium elevation.

Studies were conducted to determine whether the $Ca^{2+}$ source, calcium-calmodulin complex, activates $PLA_2$, which in turn activates NADPH oxidase, and to determine whether calcium-calmodulin inhibition suppresses heightened EC endocytosis. In these studies, EC were incubated with 240 mg/dL LDL cholesterol in the presence and absence of 10 μM W-7, a calcium-calmodulin inhibitor. It was found that W-7 significantly diminishes LDL-EC endocytotic activity. Thus, calcium-calmodulin is important to the heightened endocytosis mechanism.

The above studies in vitro demonstrated that atherogenic LDL levels induce heightened EC endocytosis and that reactive oxygen species, produced predominantly by NADPH oxidase, modulate heightened EC endocytosis. To restate, while not intending to be held to any particular theory, one may hypothesize, based on the above studies in vitro, that reactive oxygen species, generated by activated EC NADPH oxidase, modulate hypercholesterolemia-induced vascular hyperpermeability via heightened EC endocytosis.

LDL is initially and dose-dependently taken up by EC via non-specific endocytosis. When LDL is degraded in lysosomes, increasing amounts of free arachidonic acid are released into the cytoplasm. Cytoplasmic free arachidonic acid, at a threshold level, converts an inactive genetic variant of NADPH oxidase to its active form. This genetic NADPH oxidase variant generates increased amounts of reactive oxygen species which perturb the cell membrane and cause $PLA_2$ activation. $PLA_2$ activation is further enhanced by reactive oxygen species-mediated cellular $Ca^{2+}$ influx. Arachidonic acid released from membrane phospholipids markedly escalates NADPH oxidase enzyme complex recruitment and assembly. The multiple, membrane-bound, assembled enzyme complexes generate excessive quantities of reactive oxygen species, $O_2^-$ and $H_2O_2$. These reactive oxygen species increase membrane fluidity and decrease the energy of activation for endocytosis. The combination of these LDL-induced cellular events result in heightened EC endocytosis, vascular hyperpermeability, and increased transcellular transport via transcytosis. Thus, inhibition of NADPH oxidase activation with apocynin, for example, prevents heightened EC endocytosis and reduces vascular hyperpermeability.

In Vivo Apocynin Experiments

To test the foregoing hypothesis, studies were conducted in vivo, which focused on the effect of NADPH oxidase inhibition on vascular hyperpermeability using a hypercholesterolemic rabbit model. New Zealand white male rabbits were placed on a 1% cholesterol diet with (n=5) and without (n=5) 200 μg/mL apocynin added to their drinking water. After one month from commencement of feed, animals were infused with horseradish peroxidase (HRP) one minute prior to sacrifice. The aortas were excised, opened, and pinned to a dissecting tray. Gross visual inspection revealed that aortas of 1% cholesterol-fed rabbits without apocynin treatment had typical, diffuse early atherosclerotic lesions. In contrast, an absence of lesions was noted in the aortas of hypercholesterolemic rabbits treated with apocynin. Subsequently, aortas were exposed to diaminobenzidine and $H_2O_2$, and a brown reaction precipitate developed at sites of high HRP concentrations. Aortas of hypercholesterolemic rabbits without apocynin treatment had marked, diffuse areas of high HRP concentrations. However, aortas of hypercholesterolemic animals treated with apocynin consistently showed few HRP-positive areas, a pattern similar to that seen in rabbits fed normal rabbit chow. The total serum cholesterol levels of hypercholesterolemic rabbits with and without apocynin treatment were comparable.

A three month study was also carried out using ten New Zealand white male rabbits fed a 1% cholesterol diet with 30 μg/mL (n=2), 200 μg/mL (n=2), 400 μg/mL (n=2), 800 μg/mL (n=2), and without (n=2) apocynin added to their drinking water. After three months, the animals were sacrificed, and their aortas were examined as before. Visual inspection revealed that aortas of 1% cholesterol-fed rabbits without apocynin treatment had in the range of 60% of aortic surface area covered within atherosclerotic plaque. In contrast, a dose-dependent diminution of lesions was noted in the aortas of hypercholesterolemic rabbits treated with apocynin. In animals treated with 800 µg/mL of apocynin, aortic surface covered with plaque was reduced to 6%. The total serum cholesterol levels of hypercholesterolemic rabbits with and without apocynin treatment were comparable at about 1000 mg/dL.

Figure 4:
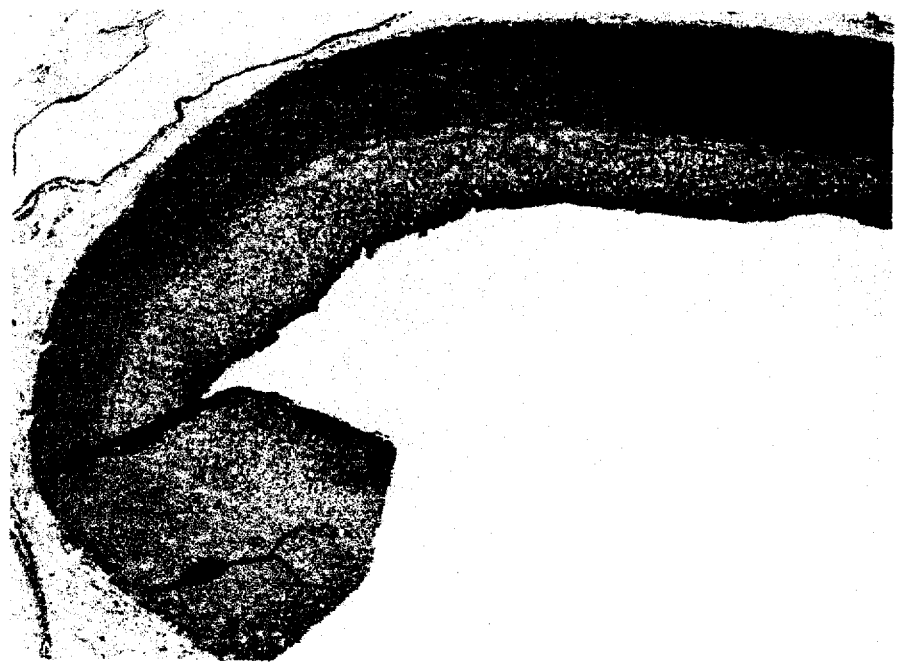
FIG. 4 is a printed reproduction of a photomicrograph of a section of abdominal aorta from a rabbit fed a high cholesterol diet.
Figure 5:
FIG. 5 is a printed reproduction of a photomicrograph of a section of abdominal aorta from a rabbit fed a high cholesterol diet and also given apocynin according to the invention.

Morphologic examination of abdominal aorta endothelium from the three-month rabbits was performed. Random tissue samples were taken from abdominal aortas of hypercholesterolemic rabbits and hypercholesterolemic rabbits treated with apocynin. Tissue samples were thin sectioned and processed for microscopy. Examination of electron and light micrographs from hypercholesterolemic rabbits without apocynin treatment revealed frequent and diffuse vascular changes characteristic of atherosclerotic disease. FIG. 4 is a representative light micrograph. In contrast, examination of multiple tissue samples from hypercholesterolemic rabbits with apocynin treatment revealed little evidence for vascular changes. FIG. 5 is a representative light micrograph. The effect of NADPH oxidase inhibition on coronary artery endothelium was similarly examined. Like the abdominal aorta, the coronary artery was found to exhibit vascular changes characteristic of atherosclerotic disease, and these changes were attenuated by treatment with apocynin.

To provide experimental evidence that apocynin reduces vascular hyperpermeability by preventing heightened EC endocytosis from occurring, the number of endocytotic vesicles on EC luminal and abluminal sides from electron micrographs were counted as an approximate measure of endocytotic activity. Electron micrographs of 50 randomly selected cells from aortas of hypercholesterolemic rabbits treated with and without apocynin were taken at 35,000× magnification. Endocytotic vesicles were counted on luminal and abluminal cell sides. Vesicles counted included those that were forming in the plasma membrane or clearly attached to the membrane. A significant decrease in the number of endocytotic vesicles in apocynin treated animals was observed, suggesting that apocynin acts by averting endocytosis increases.

Side Effects

Rabbits treated with apocynin for a one month period demonstrated no overt signs of ill health. Weight gain, over the one month period, for apocynin-treated rabbits was comparable to those animals without apocynin treatment.

One might have expected that apocynin might increase susceptibility to infections, since white blood cells use NADPH oxidase to generate $H_2O_2$ to kill bacteria ingested by phagocytosis. However, no increased incidence of infections in the white New Zealand rabbits was seen.

Another theoretical side effect of apocynin might have been thought to result from inhibition of cell proliferation. Certain tissues of the body, including bone marrow and gastrointestinal cells, have higher cell proliferation rates. Proliferating cells have been shown to have increased endocytotic activity, which likely serves to provide the necessary nutrients for cell growth. Cell growth studies showed that apocynin dose-dependently inhibited EC cell growth. At 100 µg/mL apocynin, cell proliferation rate was minimal, but visual inspection of the cells revealed no evidence of any cell injury or death for the apocynin concentrations tested.

Conclusion

The above studies in vitro and in vivo indicate that the administration of NADPH oxidase inhibitors, such as apocynin, can prevent and treat diseases associated with hyperpermeability of endothelial cells, including atherosclerosis and its related diseases. In addition to the prevention of atherosclerosis, NADPH oxidase inhibitors, such as apocynin, may be useful for the prevention and treatment of the following conditions by decreasing membrane permeability associated therewith: septic shock; post-stroke and post-MI swelling; adult respiratory distress syndrome (ARDS); hemolytic uremic syndrome; growth malignancies; reperfusion injury; post-transplant vascular changes; vasculitides; and diabetes mellitus.

The optimal dose of the NADPH oxidase inhibitor, such as apocynin, to be used in humans will vary depending upon the severity and nature of the condition to be treated, the route of administration, the age, weight, and sex of the patient, as well as on any other medications being taken by the particular patient or the existence of any complicating significant medical conditions of the patient being treated. The dose and perhaps the dose frequency will also vary according to the response of the individual patient. In general, the total daily dose range for apocynin for the conditions described herein is from about 10 mg/kg/day to about 45 mg/kg/day; for the average human, the total dose is about 500 mg to about 3000 mg daily, preferably in divided doses. In managing the patient, the therapy should be initiated at a lower dose, perhaps at about 200 mg to about 500 mg, and increased up to about 1000 mg depending on the patient's global response. It is further recommended that patients over 65 years and those with impaired renal or hepatic function initially receive low doses and that they be titrated based on individual response(s) and blood level(s). It may be necessary to use dosages outside these ranges in some cases, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to prevent" a condition are encompassed by the above-described dosage amounts and dose frequency schedule.

Any suitable route of administration may be employed for providing the patient with an effective dosage of apocynin. For example, oral, rectal, parenteral (subcutaneous, intramuscular, intravenous), transdermal, aerosol and like forms of administration may be employed. Oral dosage is preferred.

Studies on Prediction of Risk of Atherosclerosis

If a heightened endocytosis mechanism predominantly involves an endothelial cell defect rather than an atherogenic LDL type, one could explain why certain people with plasma LDL levels commonly associated with atherosclerosis do not develop atherosclerotic-related diseases. The EC defect hypothesis would also suggest that atherosclerotic patients should exhibit in common some elevation in NADPH oxidase activity.

To test the hypothesis, 92 high LDL-EC endocytosis experiments with cell isolates from 92 separate human umbilical cords were conducted in vitro. In addition, LDL preparations, isolated weekly from different human sources, were generally used on EC isolates derived from two or more human sources, thus allowing for analysis of LDL's effect. Endothelial cells from the same cord all had similar endocytotic activity with exposure to high LDL levels. In contrast, EC from different cord sources responded differently, ranging from no endocytosis change to 200–300% increases in endocytotic activity over control cells.

In 52% of EC isolates tested, high LDL exposure induced a wide variation in degree of response ranging from 5 to 300% endocytosis increases. This observation in vitro correlates with epidemiologic studies that indicate that mortality from atherosclerotic-related diseases occurs in approximately 50% of the population.

If, contrary to the EC hypothesis, an atherogenic LDL type exists, one would expect that EC isolates from multiple human sources would all have similar responses when exposed to the same LDL preparation. EC isolates tested were classified as no response (0 to 5% endocytosis increase) or response (5 to 300% endocytosis increase) and analyzed. Results showed that in only 53% of experiments did all EC isolates, exposed to the same LDL preparation, either respond or have no response. The importance of this finding is that it suggests the likelihood that the heightened endocytosis mechanism predominantly involves an EC defect rather than an atherogenic LDL type. Thus, high levels of LDL's appear to activate the heightened endocytosis mechanism.

This finding explains why certain people with plasma LDL levels commonly associated with atherosclerosis do not develop atherosclerotic-related diseases and leads to the inventive method for predicting an individual's risk of atherosclerosis. By identifying a patient having elevated NADPH oxidase activity, one can predict an increased risk of atherosclerosis. Administration of apocynin or other NAPH oxidase inhibitor can then be recommended for preventing atherosclerosis and its related diseases to those identified patients.

If genetic variants of NADPH oxidase or enzymes involved in its activation exist in the human population, and some of these variants generate excessive amounts of reactive oxygen species, this should correlate with clinical atherosclerosis. Human studies were therefore undertaken. In theses studies, the polymorphonuclear leukocyte (PMN) NADPH oxidase activity in individuals having a history of clinically documented atherosclerosis-related diseases or strong family history thereof was compared with that of individuals having no medical or family history of the diseases. Volunteers provided a medical and family history of atherosclerotic-related diseases and a venous blood sample. PMN NADPH oxidase activity was measured by flow cytometry with a fluorescent probe, using 2,7-dichlorofluorescin diacetate as indicator. NADPH oxidase activity was determined by taking fluorescent measurements from the PMN gated window. For these studies, 22 individuals with either clinically documented medical or family history of atherosclerotic-related diseases (experimental) were compared to 11 individuals (controls) with no clinical evidence of or family history of the diseases.

Figure 6:
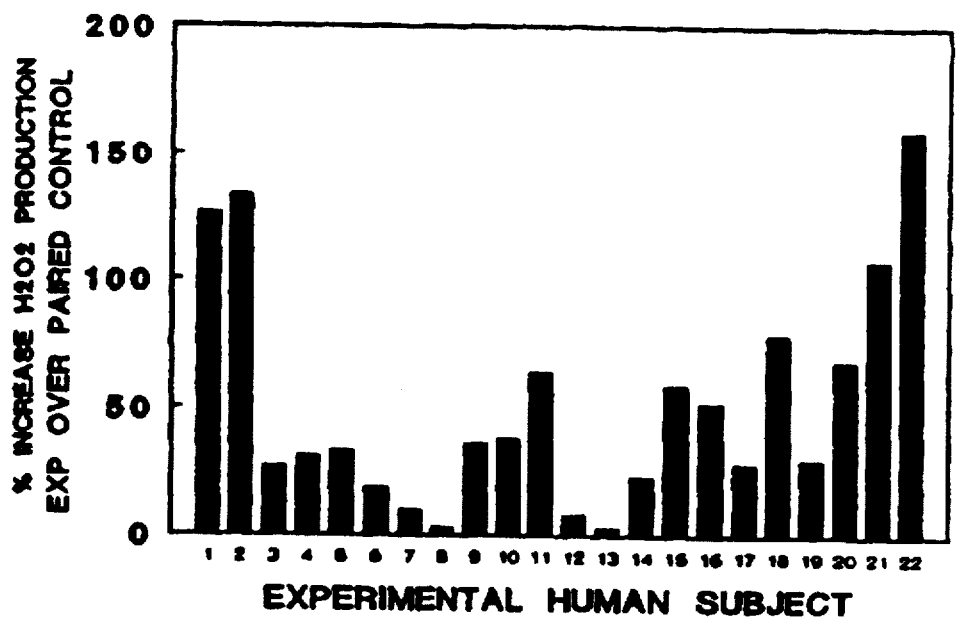
FIG. 6 is a bar graph showing the percent increase in $H_2O_2$ production (i.e. elevation of oxidase activity) for each of 22 patients with atherosclerosis compared to a paired control.

The results, as illustrated in FIG. 6, reveal that the 22 experimental human subjects had significantly increased NADPH oxidase activity over their paired controls (Probability for significance of test: $P<0.07$). The findings suggest that genetic variants of NADPH oxidase (or enzymes involved in its activation) exist, and that people with these genetic variants are at higher risk of atherosclerotic-related diseases.

While the invention has been particularly shown and described with reference to preferred embodiments thereof, it will be understood by those skilled in the art that other changes in form and details may be made therein without departing from the spirit and scope of the invention.

I claim:

1. A method for preventing atherosclerosis which comprises administering to a mammal at risk from atherosclerosis a therapeutically effective amount of an NADPH oxidase inhibitor chosen from the group consisting of catechols and o-methoxyphenols.

2. A method for inhibiting the development of an atherosclerotic plaque which comprises administering to a mammal a therapeutically effective amount of an NADPH oxidase inhibitor chosen from the group consisting of catechols and o-methoxyphenols.

3. A method for preventing atherosclerosis which comprises administering to a mammal at risk from atherosclerosis an amount of an NADPH oxidase inhibitor sufficient to inhibit heightened endothelial endocytosis in said mammal, said oxidase inhibitor chosen from the group consisting of catechols and o-methoxyphenols.

4. The method according to any of claims 1–3 wherein said NADPH oxidase inhibitor is apocynin.

5. A method of treating or preventing atherosclerosis which comprises administering to a mammal a therapeutically effective amount of apocynin.

* * * * *